(12) United States Patent
Guillemont et al.

(10) Patent No.: US 8,946,248 B2
(45) Date of Patent: Feb. 3, 2015

(54) HIV INHIBITING 5-SUBSTITUTED PYRIMIDINES

(75) Inventors: Jerôme Emile Georges Guillemont, Andé (FR); Jan Heeres, Vosselaar (BE); Paulus Joannes Lewi, Turnhout (BE)

(73) Assignee: Janssen R&D Ireland, Little Island, County Cork (IR)

(*) Notice: Subject to any disclaimer, the term of this patent is extended or adjusted under 35 U.S.C. 154(b) by 1699 days.

(21) Appl. No.: 11/576,315

(22) PCT Filed: Sep. 29, 2005

(86) PCT No.: PCT/EP2005/054932
§ 371 (c)(1),
(2), (4) Date: Jan. 21, 2008

(87) PCT Pub. No.: WO2006/035069
PCT Pub. Date: Apr. 6, 2006

(65) Prior Publication Data
US 2008/0262007 A1 Oct. 23, 2008

(30) Foreign Application Priority Data
Sep. 30, 2004 (EP) .................................. 04104805

(51) Int. Cl.
*C07D 239/48* (2006.01)
*A61K 31/505* (2006.01)
*C07D 239/50* (2006.01)

(52) U.S. Cl.
CPC ............ *C07D 239/48* (2013.01); *C07D 239/50* (2013.01)
USPC ........... 514/272; 514/275; 544/321; 544/323; 544/325

(58) Field of Classification Search
USPC ................ 544/321, 323, 325; 514/272, 275
See application file for complete search history.

(56) References Cited

U.S. PATENT DOCUMENTS

| | | |
|---|---|---|
| 3,459,731 A | 8/1969 | Gramera et al. |
| 6,593,326 B1 | 7/2003 | Bradbury et al. |
| 7,504,396 B2 | 3/2009 | Nunes et al. |
| 7,531,548 B2 | 5/2009 | Guillemont et al. |
| 2003/0036543 A1 | 2/2003 | Bebbington |
| 2005/0209221 A1 | 9/2005 | Nunes et al. |
| 2008/0262007 A1 | 10/2008 | Guillemont et al. |

(Continued)

FOREIGN PATENT DOCUMENTS

| | | |
|---|---|---|
| EP | 0 834 507 B2 | 5/2004 |
| WO | WO 97/18839 A1 | 5/1997 |

(Continued)

OTHER PUBLICATIONS

International Search Report dated Sep. 12, 2005 for related international Application No. PCT/EP2005/054932.
M. Nogradi, Dimethyl-β-Cyclodextrin, *Drugs of the Future*, 9(8):577-578, 1984.
D. Ludovici, et al., Evolution of Anti-HIV Drug Candidates. Part 3: Diarylpyrimidine (DAPY) Analogues; *Bioorganic & Medicinal Chemistry Letters*, 11:2235-2239, 2001.
In the U.S. Patent and Trademark Office, Non-Final Office Action in re: U.S. Appl. No. 12/294,692 dated Nov. 26, 2010, 8 pages.
International Search Report from. PCT/EP2005/054930, dated Jun. 20, 2006.

(Continued)

*Primary Examiner* — Deepak Rao
(74) *Attorney, Agent, or Firm* — Bernard F. Plantz

(57) ABSTRACT

HIV replication inhibitors of formula

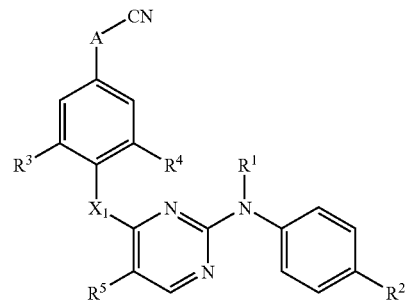

(I)

a N-oxide, a pharmaceutically acceptable addition salt, a quaternary amine or a stereochemically isomeric form thereof, wherein
A is —$CH_2$—$CH_2$—, —CH=CH—, —C≡C—;
$R^1$ is hydrogen, aryl, formyl, $C_{1-6}$alkylcarbonyl, $C_{1-6}$alkyl, $C_{1-6}$alkyloxycarbonyl,
$R^2$ hydroxy, halo, $C_{1-6}$alkyl, carboxyl, cyano, —C(=O)$R^6$, nitro, amino, mono- or di($C_{1-6}$alkyl)amino, polyhalomethyl;
$X_1$ is —$NR^1$—, —O—, —S—, —S(=O)$_p$—;
$R^3$ is H, $C_{1-6}$alkyl, halo;
$R^4$ is H, $C_{1-6}$alkyl, halo;
$R^5$ is nitro, amino, mono- and di$C_{1-4}$alkylamino, aryl, halo, —CHO, —CO—$R^6$, —COO$R^7$, —NH—C(=O)H, —NH—C(=O)$R^6$, —CH=N—O—$R^8$;
$R^6$ is $C_{1-4}$alkyl, amino, mono- or di($C_{1-4}$alkyl)amino or polyhalo$C_{1-4}$alkyl;
$R^7$ is hydrogen, $C_{1-6}$alkyl, aryl$C_{1-6}$alkyl;
$R^8$ is hydrogen, $C_{1-6}$alkyl, aryl;
p is 1 or 2;
aryl is optionally substituted phenyl; pharmaceutical compositions containing these compounds as active ingredient and processes for preparing said compounds and compositions.

15 Claims, No Drawings

(56) References Cited

U.S. PATENT DOCUMENTS

| | | |
|---|---|---|
| 2009/0181993 A1 | 7/2009 | Guillemont et al. |
| 2010/0016317 A1 | 1/2010 | Guillemont et al. |
| 2010/0168104 A1 | 7/2010 | Guillemont et al. |
| 2010/0261722 A1 | 10/2010 | Guillemont et al. |

FOREIGN PATENT DOCUMENTS

| | | | |
|---|---|---|---|
| WO | WO 99/50250 A1 | | 10/1999 |
| WO | WO 99/50256 A1 | | 10/1999 |
| WO | WO 00/27825 A1 | | 5/2000 |
| WO | WO-00/39101 A1 | | 7/2000 |
| WO | WO 01/85700 A2 | | 11/2001 |
| WO | WO 03/016306 | * | 2/2003 |
| WO | WO 03/016306 A1 | | 2/2003 |
| WO | WO-03/063794 A2 | | 8/2003 |
| WO | WO 2004/046143 A1 | | 6/2004 |
| WO | WO 2005/009443 A1 | | 2/2005 |
| WO | WO-2006/035067 A2 | | 4/2006 |
| WO | WO 2006/035069 A1 | | 4/2006 |
| WO | WO-2007/113254 A1 | | 10/2007 |
| WO | WO-2008/080964 A1 | | 7/2008 |
| WO | WO-2008/080965 A1 | | 7/2008 |

OTHER PUBLICATIONS

International Search Report from PCT/EP2007/053111, dated Aug. 14, 2007.
International Search Report from PCT/EP2007/064605, dated May 6, 2008.
International Search Report from PCT/EP2007/064606, dated Jul. 14, 2008.
Vippagunta, S. et al., "Crystalline solids, " *Advanced Drug Delivery Reviews*, 2001; 48: 3-26.
In the United States Patent and Trademark Office, Final-Office Action in re: U.S. Appl. No. 11/575,818, dated Feb. 2, 2011, 6 pages.
In the United States Patent and Trademark Office, Final-Office Action in re: U.S. Appl. No. 12/294,692, dated May 13, 2011, 10 pages.
In the United States Patent and Trademark Office, Final-Office Action in re: U.S. Appl. No. 12/521,189, dated Apr. 10, 2012, 11 pages.
In the United States Patent and Trademark Office, Non-Final-Office Action in re: U.S. Appl. No. 11/575,818, dated Aug. 5, 2010, 7 pages.
In the United States Patent and Trademark Office, Non-Final-Office Action in re: U.S. Appl. No. 12/521,189, dated Sep. 23, 2011, 15 pages.
In the United States Patent and Trademark Office, Non-Final-Office Action in re: U.S. Appl. No. 12/521,379, dated Sep. 26, 2011, 8 pages.

* cited by examiner

HIV INHIBITING 5-SUBSTITUTED PYRIMIDINES

CROSS REFERENCE TO RELATED APPLICATIONS

This application is a national stage application of Patent Application No. PCT/EP2005/054932, filed Sep. 29, 2005, which application claims priority from EPO Patent Application No. 04104805.9, filed Sep. 30, 2004, both of which are hereby incorporated by reference in their entirety.

The present invention is concerned with pyrimidine derivatives having HIV (Human Immunodeficiency Virus) replication inhibiting properties. The invention further relates to methods for their preparation and pharmaceutical compositions comprising them. The invention also relates to the use of said compounds in the prevention or the treatment of HIV infection.

Resistance of the HIV virus against currently available HIV drugs continues to be a major cause of therapy failure. This has led to the introduction of combination therapy of two or more anti-HIV agents usually having a different activity profile. Significant progress was made by the introduction of HAART therapy (Highly Active Anti-Retroviral Therapy), which has resulted in a significant reduction of morbidity and mortality in HIV patient populations treated therewith. HAART involves various combinations of nucleoside reverse transcriptase inhibitors (NRTIs), non-nucleoside reverse transcriptase inhibitors (NNRTIs) and protease inhibitors (PIs). Current guidelines for antiretroviral therapy recommend such triple combination therapy regimen for initial treatment. However, these multidrug therapies do not completely eliminate HIV and long-term treatment usually results in multidrug resistance. In particular, half of the patients receiving anti-HIV combination therapy do not respond fully to the treatment, mainly because of resistance of the virus to one or more drugs used. It also has been shown that resistant virus is carried over to newly infected individuals, resulting in severely limited therapy options for these drug-naive patients.

Therefore there is a continued need for new combinations of active ingredients that are effective against HIV. New types of anti-HIV effective active ingredients, differing in chemical structure and activity profile are useful in new types of combination therapy Finding such active ingredients therefore is a highly desirable goal to achieve.

The present invention is aimed at providing particular novel series of pyrimidine derivatives having HIV replication inhibiting properties. WO 99/50250, WO 00/27825 and WO 01/85700 disclose certain substituted aminopyrimidines and WO 99/50256 and EP-834 507 disclose aminotriazines having HIV replication inhibiting properties.

The compounds of the invention differ from prior art compounds in structure, pharmacological activity and/or pharmacological potency. It has been found that the introduction of certain substituents in the 5-position of specifically substituted pyrimidines results in compounds the compounds not only acting favorably in terms of their capability to inhibit the replication of Human Immunodeficiency Virus (HIV), but also by their improved ability to inhibit the replication of mutant strains, in particular strains which have become resistant to one or more known NNRTI drugs (Non Nucleoside Reverse Transcriptase Inhibitor drugs), which strains are referred to as drug or multidrug resistant HIV strains.

Thus in one aspect, the present invention concerns compounds of formula

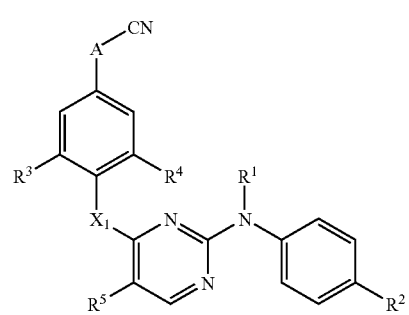

the N-oxides, pharmaceutically acceptable addition salts, quaternary amines or stereochemically isomeric forms thereof, wherein A is —$CH_2$—$CH_2$—, —CH=CH—, —C≡C—;

each $R^1$ independently is hydrogen, aryl, formyl, $C_{1-6}$alkylcarbonyl, $C_{1-6}$alkyl, $C_{1-6}$alkyloxycarbonyl;

$R^2$ is hydroxy, halo, $C_{1-6}$alkyl, carboxyl, cyano, —C(=O)$R^6$, nitro, amino, mono- or di($C_{1-6}$ alkyl)amino, polyhalomethyl;

$X_1$ is —$NR^1$—, —O—, —S—, —S(=O)$_p$—;

$R^3$ is H, $C_{1-6}$alkyl, halo;

$R^4$ is H, $C_{1-6}$alkyl, halo;

$R^5$ is nitro, amino, mono- and di$C_{1-4}$alkylamino, aryl, halo, —CO—H, —CO—$R^6$, —COO$R^7$, —NH—C(=O)H, —NH—C(=O)$R^6$, —CH=N—O—$R^8$;

$R^6$ is $C_{1-4}$alkyl, amino, mono- or di($C_{1-4}$alkyl)amino, or polyhalo$C_{1-4}$alkyl;

$R^7$ is hydrogen, $C_{1-6}$alkyl, aryl$C_{1-6}$alkyl;

$R^8$ is hydrogen, $C_{1-6}$alkyl, aryl;

each p is 1 or 2;

each aryl is phenyl or phenyl substituted with one, two, three, four or five substituents each independently selected from halo, hydroxy, mercapto, $C_{1-6}$alkyl, hydroxy-$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{1-2}$alkyl defines methyl or ethyl; $C_{3-7}$cycloalkyl is generic to cyclopropyl, cyclobutyl, cyclopentyl, cyclohexyl and cycloheptyl. Preferred amongst $C_{1-6}$alkyl are $C_{1-4}$alkyl or $C_{1-2}$alkyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The terms carboxyl, carboxy or hydroxycarbonyl refer to a group —COOH.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, fluoromethyl, difluoromethyl or trifluoromethyl; polyhaloC$_{1-4}$alkyl or polyhaloC$_{1-6}$alkyl as a group or part of a group is defined as mono- or polyhalo-substituted C$_{1-4}$alkyl or C$_{1-6}$alkyl, for example, the groups defined in halomethyl, 1,1-difluoro-ethyl, 2,2,2-trifluorethyl, pentafluoroethyl and the like. In case more than one halogen atoms are attached to an alkyl group within the definition of polyhalomethyl, polyhaloC$_{1-4}$alkyl or polyhaloC$_{1-6}$alkyl, they may be the same or different.

Whenever it occurs in the definition of the compounds of formula (I) or in any of the subgroups specified herein, each aryl independently is as specified above in the definition of the compounds of formulas (I) or in the more restricted definitions of aryl as specified hereinafter.

When any variable occurs more than one time in any radical, each definition of such variable is independent.

Any of the restrictions in the definitions of the radicals herein are meant to be applicable to the group of compounds of formula (I) as well as to any subgroup defined or mentioned herein.

Lines drawn from substituents into ring systems indicate that the bond may be attached to any of the suitable ring atoms.

For therapeutic use, salts of the compounds of formula (I) are those wherein the counter ion is pharmaceutically acceptable. However, salts of acids and bases, which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethyl-amine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form. The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms, which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer. In particular, stereogenic centers may have the R- or S-configuration; substituents on bivalent cyclic (partially) saturated radicals may have either the cis- or trans-configuration.

Compounds having double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are meant to be embraced within the scope of this invention.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I), which are stereochemically pure.

Particular subgroups of compounds of formula (I) or any of the subgroups of compounds of formula (I) specified herein which are the non-salt-forms, the salts, the N-oxide forms and stereochemically isomeric forms. Of interest amongst these are the non-salt-forms, the salts and stereochemically isomeric forms. As used herein, the term 'non-salt-form' refers to the form of a compound which is not a salt, which in most cases will be the free base form.

Whenever mention is made hereinbefore or hereinafter that substituents can be selected each independently out of a list of numerous definitions, such as for example for $R^9$ and $R^{10}$, all possible combinations are intended which are chemically possible or which lead to chemically stable molecules.

It is to be understood that any of the subgroups of compounds of formulae (I) as defined herein, are meant to also comprise any prodrugs, N-oxides, addition salts, quaternary amines, metal complexes and stereochemically isomeric forms of such compounds.

Particular subgroups of the compounds of formula (I) are those compounds of formula (I), or any subgroup of compounds of formula (I) specified herein, wherein
(a) A is —$CH_2$—$CH_2$— or —CH=CH—; or wherein (b) A is —CH=CH—.

Further subgroups of the compounds of formula (I) are those compounds of formula (I), or any subgroup of compounds of formula (I) specified herein, wherein
(a) $R^1$ is hydrogen, formyl, $C_{1-6}$alkylcarbonyl, $C_{1-6}$alkyl, $C_{1-6}$alkyloxycarbonyl;
(b) $R^1$ is hydrogen, $C_{1-6}$alkyl;
(c) $R^1$ is hydrogen, methyl;
(d) $R^1$ is hydrogen.

Further subgroups of the compounds of formula (I) are those compounds of formula (I), or any subgroup of compounds of formula (I) specified herein, wherein (a) $R^2$ is cyano, aminocarbonyl; or wherein (b) $R^2$ is cyano.

Further subgroups of the compounds of formula (I) are those compounds of formula (I), or any subgroup of compounds of formula (I) specified herein, wherein
(a) $X_1$ is —$NR^1$—, —O—;
(b) $X_1$ is —$NR^1$—,
(c) $X_1$ is —NH—, —N($C_{1-4}$alkyl)—, —O—;
(d) $X_1$ is —NH—, —N($CH_3$)—, —O—;
(e) $X_1$ is —NH—, —N($C_{1-4}$alkyl)—;
(f) $X_1$ is —NH—, —N($CH_3$)—; or
(g) $X_1$ is —NH—.

Other subgroups of the compounds of formula (I) are those compounds of formula (I), or any subgroup of compounds of formula (I) specified herein, wherein
(a) $R^3$ is H, $C_{1-6}$alkyl, halo; (b) $R^3$ is H, $C_{1-4}$alkyl, halo; (c) $R^3$ is H, fluoro, chloro, bromo, methyl; (d) $R^3$ is H, methyl; or wherein (e) $R^3$ is methyl.

Still other subgroups of the compounds of formula (I) are those compounds of formula (I), or any subgroup of compounds of formula (I) specified herein, wherein
(a) $R^4$ is H, $C_{1-6}$alkyl, halo; (b) $R^4$ is H, $C_{1-4}$alkyl, halo; (c) $R^4$ is H, fluoro, chloro, bromo, methyl; (d) $R^4$ is H, methyl; (e) $R^4$ is methyl.

Still other subgroups of the compounds of formula (I) are those compounds of formula (I), or any subgroup of compounds of formula (I) specified herein, wherein
(a) $R^5$ is nitro;
(b) $R^5$ is amino, mono- and di $C_{1-4}$alkylamino, —NH—C(=O)H, —NH—C(=O)$R^6$;
(c) $R^5$ is amino, mono- and di $C_{1-4}$alkylamino;
(d) $R^5$ is aryl;
(e) $R^5$ is halo;
(f) $R^5$ is —CO—H, —CO—$R^6$, —COO$R^7$;
(g) $R^5$ is —CO—H;
(h) $R^5$ is —CO—$R^6$;
(i) $R^5$ is —COO$R^7$;
(j) $R^5$ is —CH=N—O—$R^8$.

Still other subgroups of the compounds of formula (I) are those compounds of formula (I), or any subgroup of compounds of formula (I) specified herein, wherein
(a) $R^6$ is $C_{1-4}$alkyl, amino, mono- or di($C_{1-4}$alkyl)amino;
(b) $R^6$ is $C_{1-4}$alkyl, amino or dimethylamino;
(c) $R^6$ is methyl, amino, mono- or dimethylamino;

(d) $R^6$ is amino or dimethylamino;
(e) $R^6$ is methyl, amino or mono- or dimethylamino, polyhalomethyl.

Still other subgroups of the compounds of formula (I) are those compounds of formula (I), or any subgroup of compounds of formula (I) specified herein, wherein
(a) $R^7$ is hydrogen, $C_{1-4}$alkyl; or wherein (b) $R^7$ is hydrogen or $C_{1-2}$alkyl.

Still other subgroups of the compounds of formula (I) are those compounds of formula (I), or any subgroup of compounds of formula (I) specified herein, wherein
(a) $R^8$ is hydrogen, $C_{1-4}$alkyl; or wherein (b) $R^8$ is hydrogen or $C_{1-2}$alkyl.

Other subgroups of the compounds of formula (I) are those compounds of formula (I), or any subgroup of compounds of formula (I) specified herein, wherein
(a) aryl is phenyl or phenyl substituted with one, two or three substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl.
(b) aryl is phenyl or phenyl substituted with one, two or three substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, trifluoromethyl, trifluoromethoxy, aminocarbonyl.
(c) aryl is phenyl or phenyl substituted with one, two or three substituents each independently selected from halo, hydroxy, $C_{1-6}$alkyl, hydroxy$C_{1-6}$alkyl, amino$C_{1-6}$alkyl, mono or di($C_{1-6}$alkyl)amino $C_{1-6}$alkyl, $C_{1-6}$alkylcarbonyl, $C_{1-6}$alkyloxy, $C_{1-6}$alkyloxycarbonyl, cyano, nitro, trifluoromethyl.
(d) aryl is phenyl or phenyl substituted with one, two or three substituents each independently selected from halo, hydroxy, $C_{1-6}$alkyl, $C_{1-6}$alkyloxy, cyano, nitro, trifluoromethyl.

Of particular interest are those compounds of formula (I) or any of the subgroups of compounds of formula (I) wherein A is —CH=CH— and wherein the substituents on A are in an E-configuration (i.e. so-called 'E'-isomers).

The compounds of formula (J) can be prepared by reacting an intermediate of formula (II) wherein $W_1$ represents a suitable leaving group, such as for example halogen, e.g. chloro, bromo, a tosyl, mesyl and the like groups, with an intermediate of formula (III).

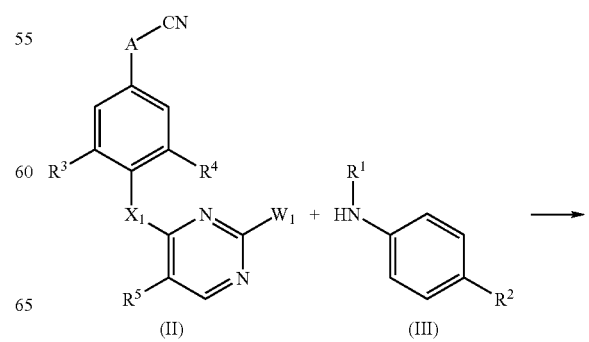

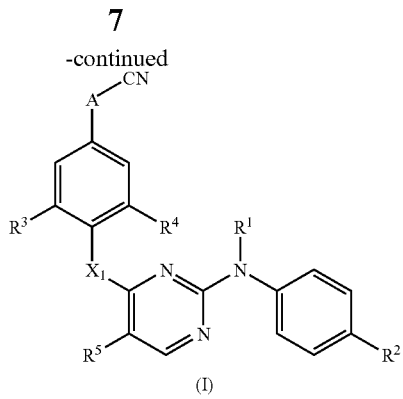

The reaction of the pyrimidine derivative (II) with the amine (III) is typically conducted in the presence of a suitable solvent. Suitable solvents are for example an alcohol, such as for example ethanol, 2-propanol; a dipolar aprotic solvent such as acetonitrile, N,N-dimethylformamide; N,N-dimethylacetamide, 1-methyl-2-pyrrolidinone; an ether such as tetrahydrofuran, 1,4-dioxane, propylene glycol monomethylether. The reaction can be done under acid conditions obtained by adding amounts of a suitable acid such as for example camphor sulfonic acid, or by using acid solvents, e.g. hydrochloric acid dissolved in an alkanol such as 1- or 2-propanol.

The compounds of formula (I) can also be prepared by forming the $X_1$ linkage by either reacting (IV-a) with (V-a) or (IV-b) with (V-b) as outlined in the following scheme.

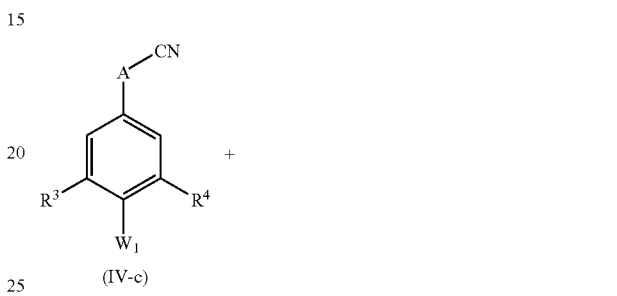

In this reaction scheme $W_1$ represents an appropriate leaving group, which in particular is as specified above.

In particular, compounds of formula (I) wherein $X_1$ represents $NR^1$, said compounds being represented by formula (I-a), can be prepared by reacting an intermediate of formula (IV-c), wherein $W_1$ is an appropriate leaving group, e.g. chloro or bromo, with an intermediate of formula (V-c). The leaving group $W_1$ may also be introduced in situ, e.g. by converting the corresponding hydroxy function into a leaving group for example by $POCl_3$. The reaction of (IV-c) with (V-c) preferably is conducted in a suitable solvent in the presence of a base, e.g. triethylamine. Suitable solvents are for example acetonitrile, alcohols, such as for example ethanol, 2-propanol, ethylene glycol, propylene glycol, polar aprotic solvents such as N,N-dimethylformamide; N,N-dimethylacetamide, dimethylsufoxide, 1-methyl-2-pyrrolidinone, [bmim]$PF_5$; ethers such as 1,4-dioxane, propylene glycol monomethylether.

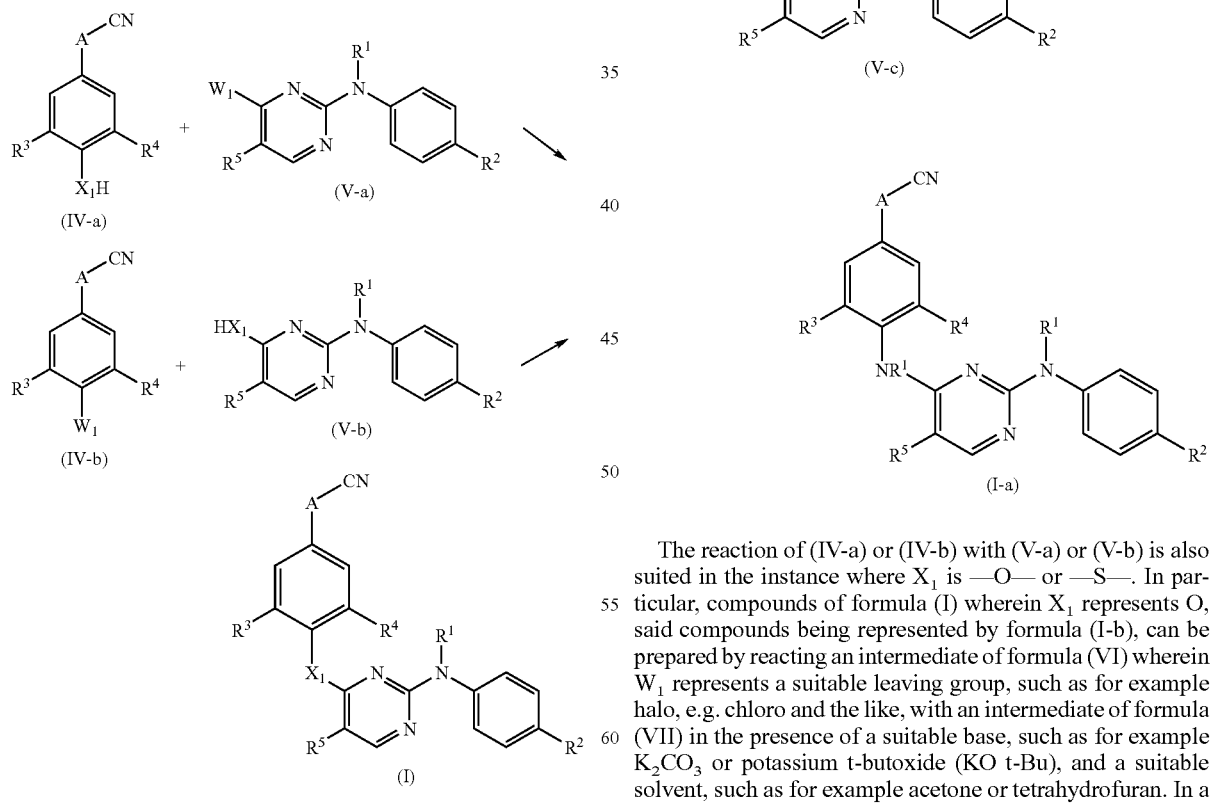

The reaction of (IV-a) or (IV-b) with (V-a) or (V-b) is also suited in the instance where $X_1$ is —O— or —S—. In particular, compounds of formula (I) wherein $X_1$ represents O, said compounds being represented by formula (I-b), can be prepared by reacting an intermediate of formula (VI) wherein $W_1$ represents a suitable leaving group, such as for example halo, e.g. chloro and the like, with an intermediate of formula (VII) in the presence of a suitable base, such as for example $K_2CO_3$ or potassium t-butoxide (KO t-Bu), and a suitable solvent, such as for example acetone or tetrahydrofuran. In a particular execution, intermediate (VII) is first reacted under stirring at room temperature with a suitable metal hydride in an organic solvent. Subsequently, an intermediate (VI), wherein —$W_1$ is a suitable leaving group or a precursor of a leaving group, is added.

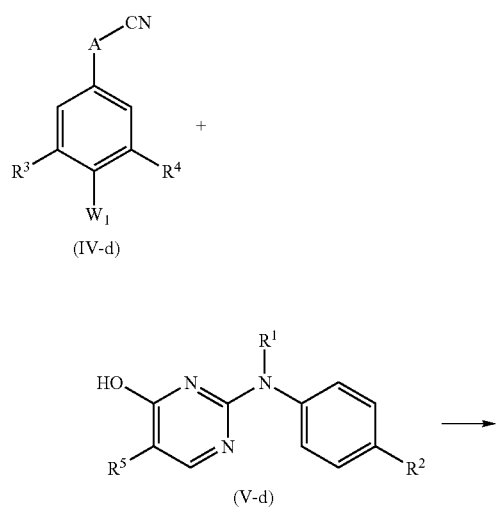

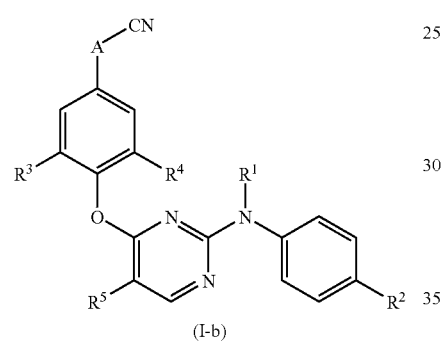

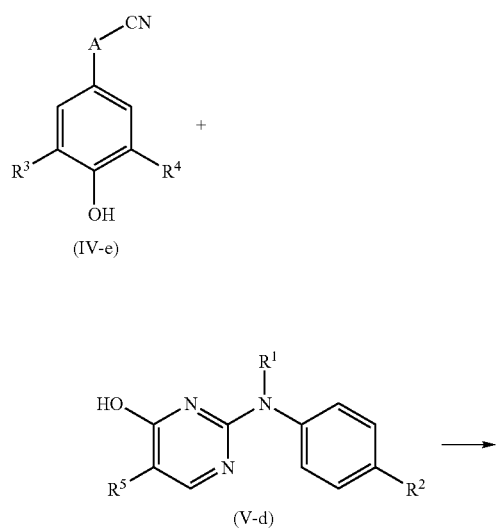

Compounds of formula (I-b) can also be prepared by reacting an intermediate of formula (IV-e) with an intermediate of formula (V-d) in the presence of POCl₃, a suitable base, such as for example K₂CO₃ or potassium t-butoxide (KO t-Bu), and a suitable solvent, such as for example acetone or tetrahydrofuran.

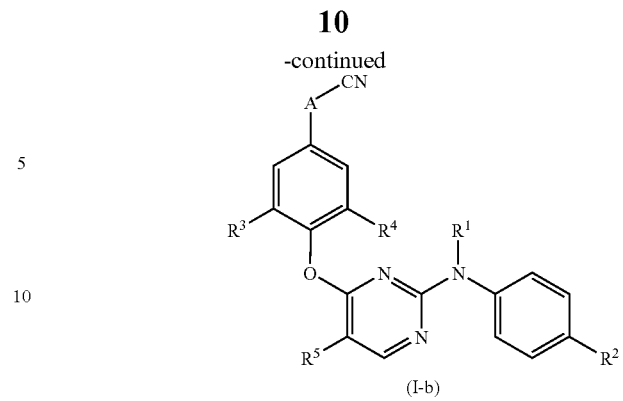

The thio-compounds (X₁ is —S—) can be obtained in a similar manner and can conveniently be transferred to the corresponding sulfoxide or sulfone using art-known oxidation procedures.

The compounds of formula (I-c), which are compounds of formula (I) wherein R⁵ is aryl, can also be prepared by reacting a compound (I-d) wherein W₁ represents a suitable leaving group, such as for example halogen, e.g. chloro, bromo, with an aryl radical with special groups such as boronic acid (i.e. —B(OH)₂) or borate esters (i.e. —B(OR)₂ wherein R is alkyl or alkylene, e.g. R is methyl, ethyl or ethylene). This type of reaction can be typically conducted in the presence of a copper salt, in particular copper(II) acetate, and a suitable quencher like pyridine may be added to the reaction mixture.

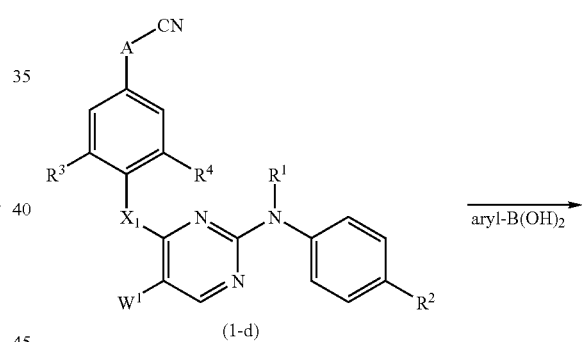

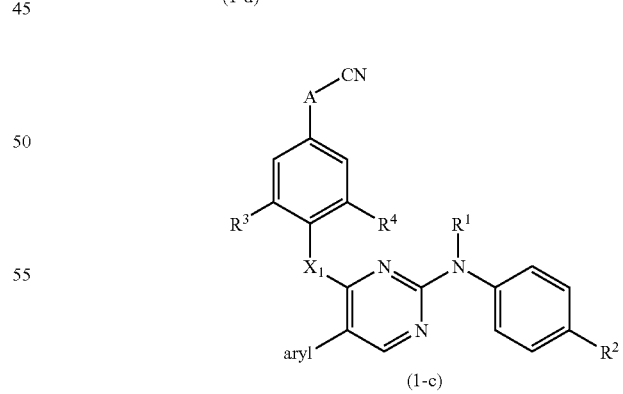

The compounds (I-d-1) which are compounds of formula (I-d) wherein W¹ is halo are prepared for example by halogenating a corresponding starting material of formula (VI) which can be prepared as described in WO-03/016306. Other leaving groups can be introduced by replacing the halo group using suitable reagents.

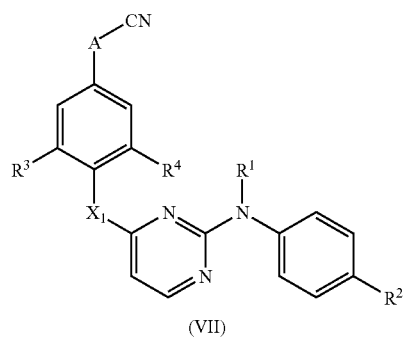

(VII)

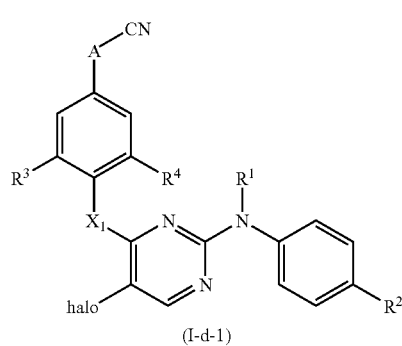

(I-d-1)

The compounds (I-d-1) can be converted in the corresponding compounds (I-e), which have a group —COOR in the 5-position of the pyrimidine moiety. The compounds (I-e) in turn can be converted in the corresponding amides (1-f).

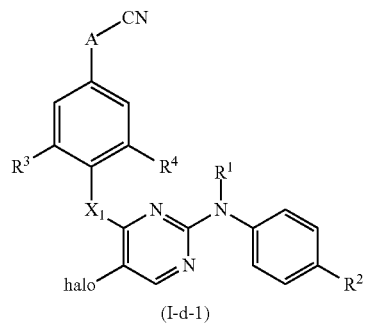

(I-d-1)

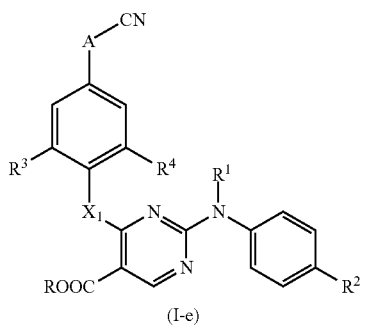

(I-e)

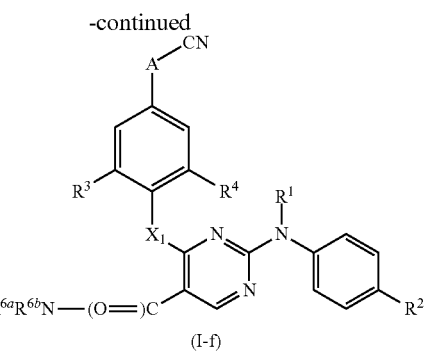

(I-f)

The compounds (I-g), which are compounds of formula (I) wherein $R^5$ is a nitro group, can be converted by a nitro to amino reduction in the corresponding compounds (I-h), which have an amino group in the 5-position of the pyrimidine moiety. The compounds (I-h) in turn can be converted in the corresponding amides (I-i) using an appropriate acylation reaction.

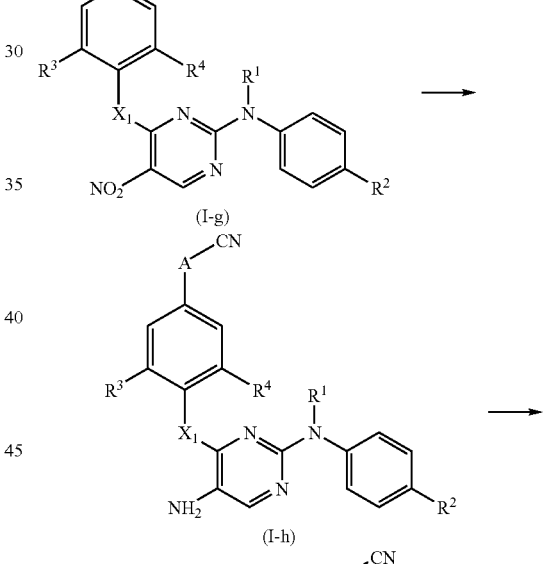

The compounds of formula (I-j), which are compounds of formula (I) wherein $R^5$ is —CHO can be prepared by reacting compounds (I-d-1) with pressurized CO gas in the presence of sodium formate and a suitable catalyst, e.g. dichlorobis(triphenyl-phosphine)-palladium(II).

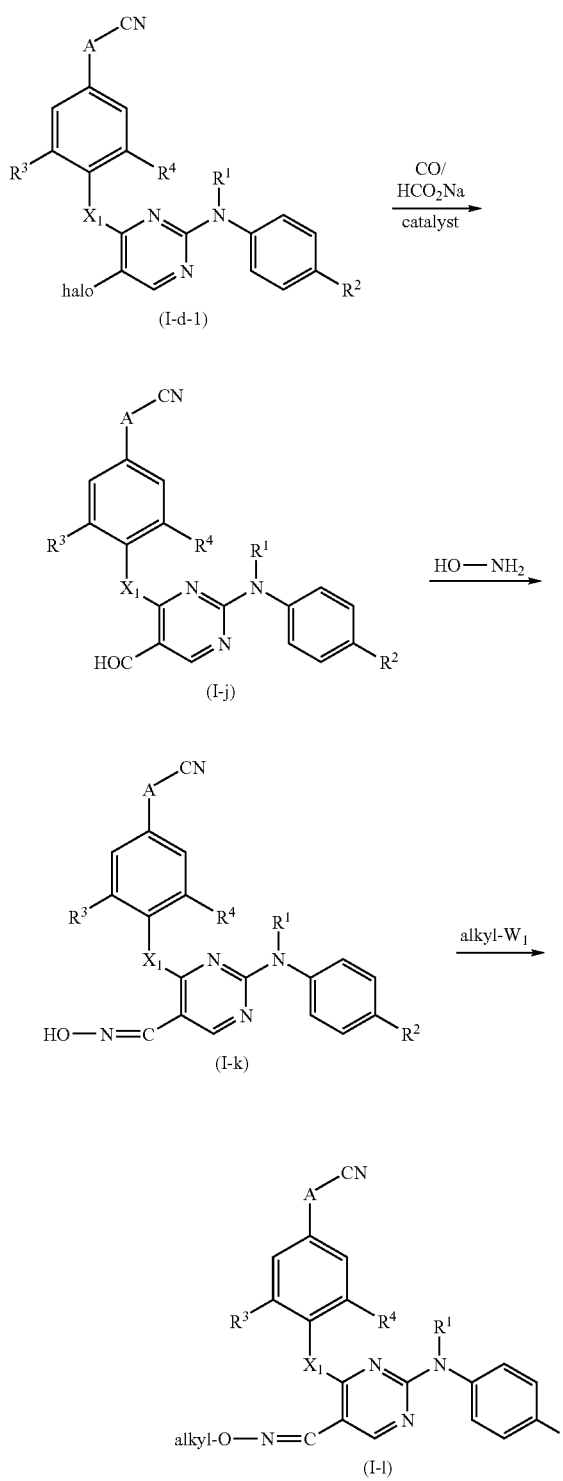

The compounds (I-j) can be reacted with hydroxylamine to compounds (I-k) which in turn can be alkylated to yield compounds (I-l) wherein $R^5$ is an alkylated oxime. The compounds (I-j) can also be converted directly to compounds (I-l) by reacting the starting compounds (I-j) with an alkyl hydroxylamine.

The compounds of formula (I) may further be prepared by converting compounds of formula (I) into each other according to art-known group transformation reactions. The compounds of formula (I) may be converted to the corresponding N-oxide forms following art-known procedures for converting a tertiary nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^3$ or $R^4$ is hydrogen, can be converted into a compounds of formula (I) wherein $R^3$ or $R^4$ represents halo, by reaction with a suitable halo-introducing agent, such as for example N-chlorosuccinimide or N-borosuccinimide, or a combination thereof, in the presence of a suitable solvent, such as for example acetic acid.

Compounds of formula (I) wherein $R^1$ represents $C_{1-6}$alkyloxycarbonyl, can be converted into a compound of formula (I) wherein $R^1$ represents hydrogen, by reaction with a suitable base, such as for example sodium hydroxide or methoxide. Where $R^1$ is t.butyloxycarbonyl, the corresponding compounds wherein $R^1$ is hydrogen can be made by treatment with trifluoroacetic acid.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

Intermediates of formula (II) can be prepared by reacting an intermediate of formula (VIII) wherein $W_1$ is defined as hereinabove, with an intermediate of formula (IX) in the presence of a suitable solvent, such as for example tetrahydrofuran, and optionally in the presence of a suitable base, such as for example $Na_2CO_3$.

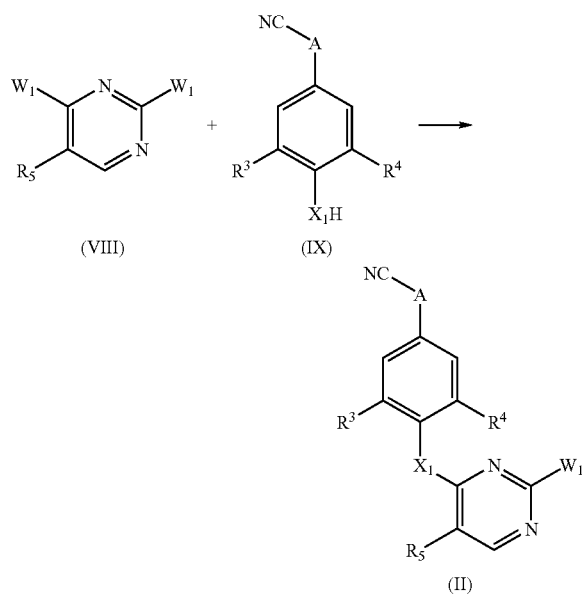

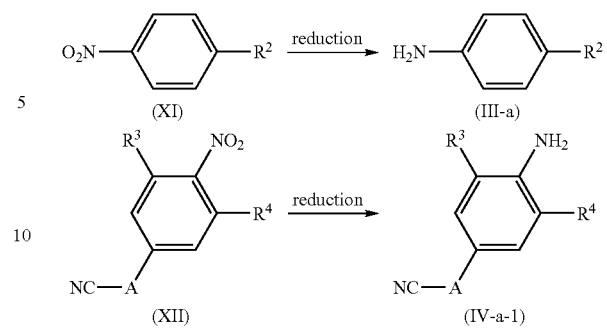

Intermediates of formula (III-a) wherein A represents —CH$_2$—CH$_2$—, said intermediates being represented by formula (III-a-1), can be prepared by reacting an intermediate of formula (XII-a) with Pd/C in the presence of a suitable solvent, such as for example an alcohol, e.g. ethanol and the like.

Intermediates of formula (VIII) can be prepared in accordance with art-known procedures.

The intermediates (V-a) and (V-b) can be prepared as follows

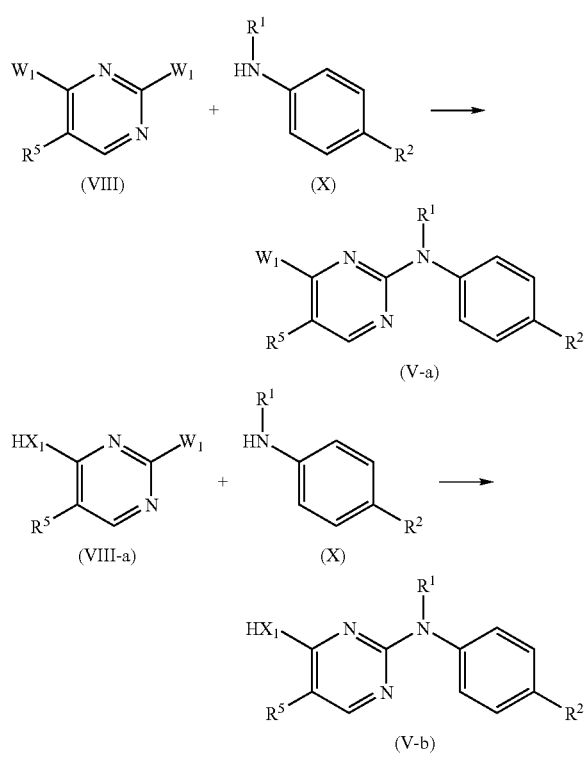

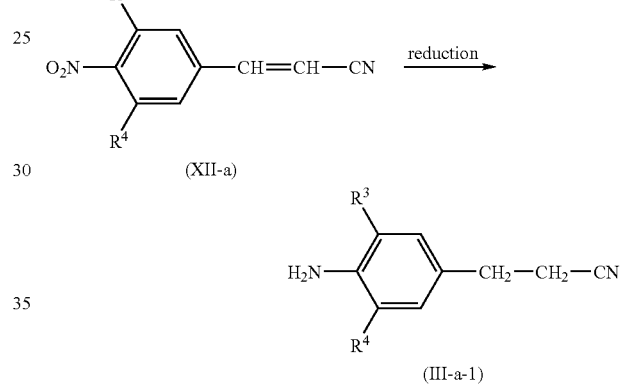

Intermediates of formula (III) or (IV-a) wherein R$^1$ is hydrogen or X$_1$ is NH, said intermediates being represented by formula (III-a) and (IV-a-1), can be prepared by reacting an intermediate of formula (XI) or (XII) with a suitable reducing agent, such as Fe, in the presence of NH$_4$Cl and a suitable solvent, such as for example tetrahydrofuran, H$_2$O and an alcohol, e.g. methanol and the like.

Intermediates of formula (XII-a), can be prepared by reacting an intermediate of formula (XIII) with diethylcyanomethylphosphonate in the presence of a suitable base, such as for example NaOCH$_3$, and a suitable solvent, such as for example tetrahydrofuran.

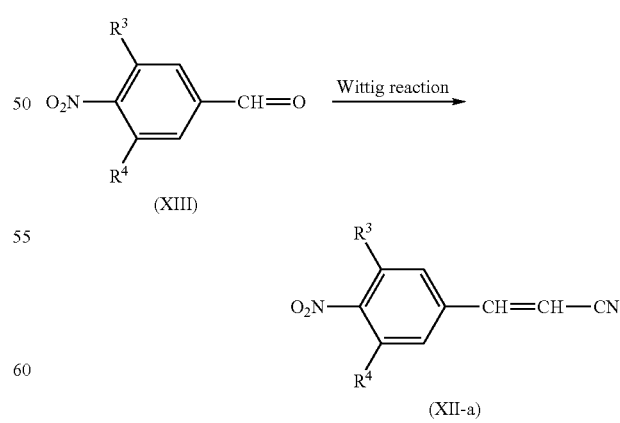

Intermediates of formula (XIII) can be prepared by reacting an intermediate of formula (XIV) with a suitable oxidizing agent, such as for example MnO$_2$, in the presence of a suitable solvent, such as for example acetone.

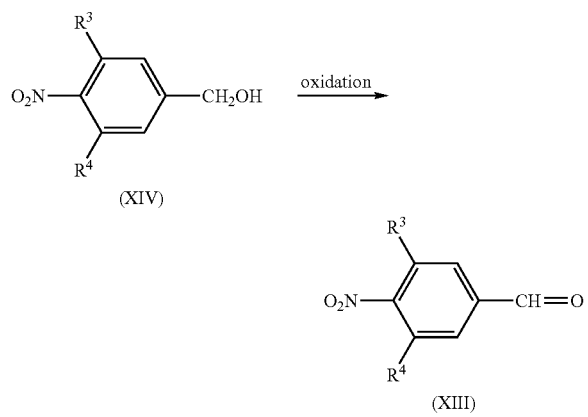

Intermediates of formula (XIV) can be prepared by reacting an intermediate of formula (XV) with NaBH$_4$ in the presence of ethylchloroformate, a suitable base, such as for example N,N-diethylethanamine, and a suitable solvent, such as for example tetrahydrofuran.

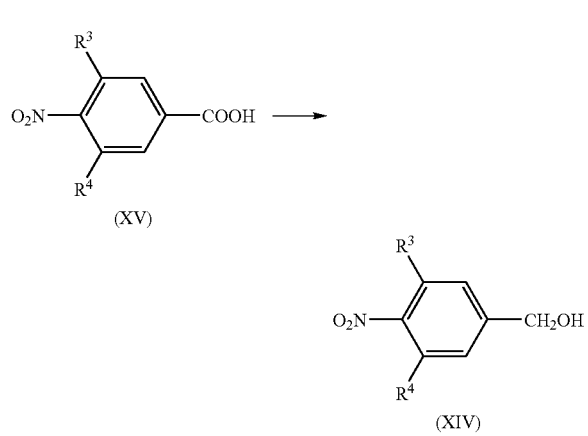

Intermediates of formula (XI) and (XII) can be prepared by reacting an intermediate of formula (XVI) respectively (XVII) with HNO$_3$, NaNO$_3$ or KNO$_3$ in the presence of H$_2$SO$_4$, AcOH or CH$_3$SO$_3$H.

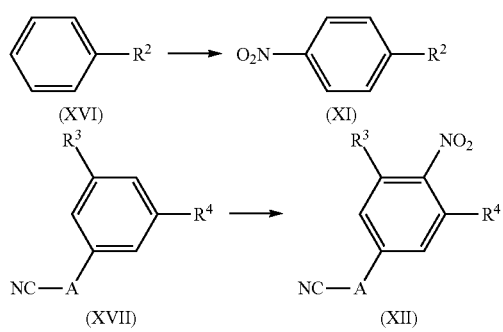

Intermediates of formula (V-b) wherein X$_1$ is O and R$^5$ is bromo, said intermediate being represented by formula (V-b-1), can be prepared from intermediates (XVIII) by reaction with Br$_2$ in the presence of a suitable base, such as for example N,N-diethylethanamine, and a suitable solvent, such as for example dimethylsulfoxide.

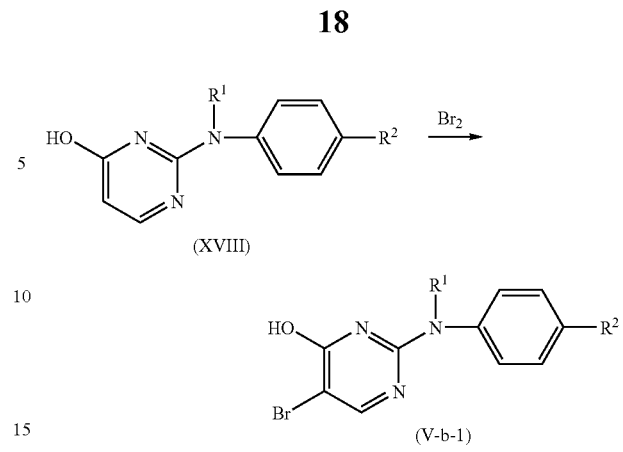

Intermediates of formula (V-b-1) can be converted into an intermediate of formula (V-a) wherein R$^5$ and W$_1$ represent chloro, said intermediate being represented by formula (V-a-1), by reaction with POCl$_3$.

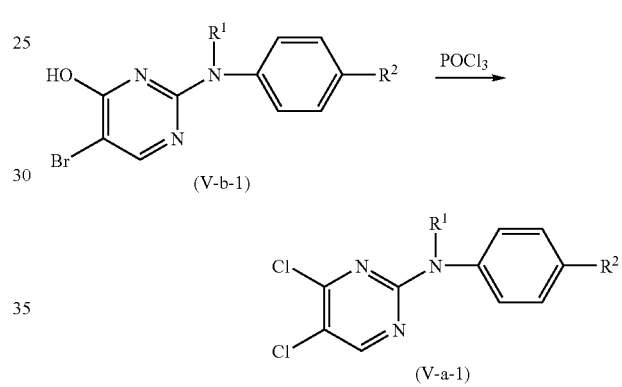

Intermediates of formula (III-a), wherein A is —CH═CH— and X$_1$ is NH or O, said intermediates being represented by formula (III-a-2) respectively (III-a-3), may also be prepared from an intermediate of formula (XIX) respectively (XX) by reaction with H$_2$C═CH—CN in the presence of Pd(OAc)$_2$, P(o-Tol)$_3$, a suitable base, such as for example N,N-diethylethanamine, and a suitable solvent, such as for example CH$_3$—CN.

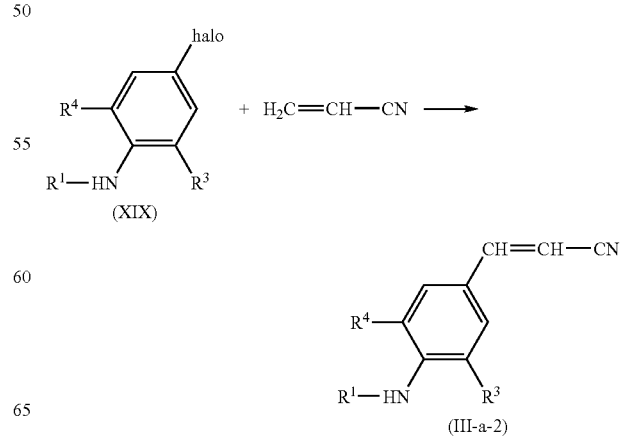

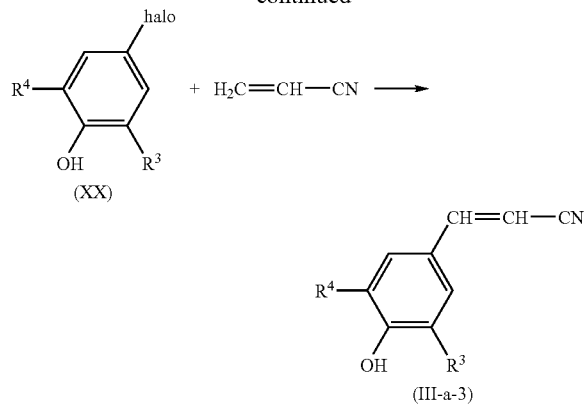

The compounds of formula (I) show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defence system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy-$C_{1-6}$alkyl, particularly hydroxyethyl, hydroxy-propyl or hydroxybutyl; carboxy-$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions, which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps
 a) dissolving the compound of formula (I) and the water-soluble polymer in an appropriate solvent, optionally at elevated temperatures;
 b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
 a) mixing a compound of formula (I) and an appropriate water-soluble polymer,
 b) optionally blending additives with the thus obtained mixture,
 c) heating and compounding the thus obtained blend until one obtains a homogenous melt,
 d) forcing the thus obtained melt through one or more nozzles; and
 e) cooling the melt until it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water-soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl-$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as antivirals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transcriptase inhibitors such as nevirapine (11-cyclopropyl-5,11-di-hydro-4-methyl-6H-dipyrido-[3,2-b: 2',3'-e][1,4]diazepin-6-one), efavirenz, delavirdine, TMC-120, TMC-125 and the like; phosphonate reverse transcriptase inhibitors, e.g. tenofovir and the like; compounds of the TIBO (tetrahydroimidazo-[4,5,1-jk][1,4]-benzodiazepine-2(1H)-one and thione)-type e.g. (S)-8-chloro-4,5,6,7-tetrahydro-5-methyl-6-(3-methyl-2-butenyl) imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithio-carbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

The following examples are intended to illustrate the present invention.

EXAMPLES

Hereinafter, "DMSO" is defined as dimethylsulfoxide, "TFA" is defined as trifluoroacetic acid, "DMF" is defined as N,N-dimethylformamide and "THF" is defined as tetrahydrofuran.

Example 1

Preparation of Compound 1

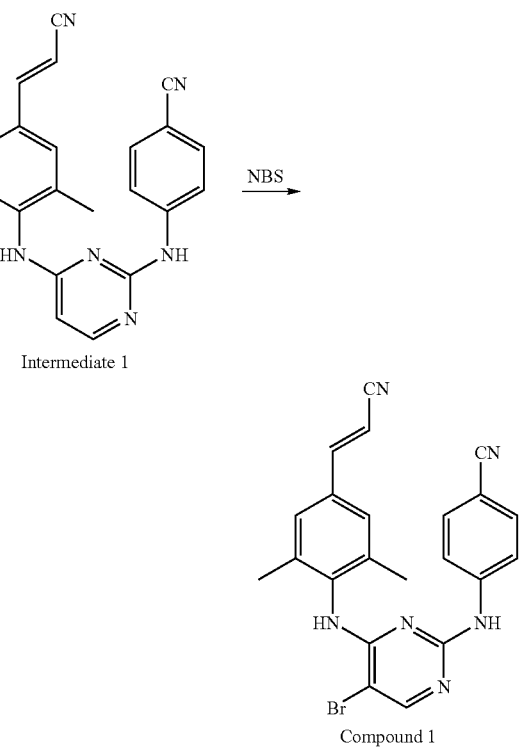

N-bromosuccinimide (0.0393 mol) was added portion wise at room temperature to Intermediate 1 (0.0327 mol), the preparation of which is described in WO-03/016306, in CH₃CN (100 ml). The mixture was stirred at room temperature for 4 hours. The precipitate was filtered off, washed with CH₃CN and dried yielding 10.08 g of the desired end product. The filtrate was evaporated and purified by column chromatography (eluent: CH₂Cl₂ 100; 35-70 μm). The pure fractions were collected, the solvent was evaporated and the residue was crystallized from CH₃CN. Yield: 2.4 g of Compound 1. The two fractions were collected. Yield: 12.48 g of Compound 1 (86%, melting point: >250° C.).

Example 2

Preparation of Compound 2

Compound 2

N-chlorosuccinimide (0.000327 mol) was added portion wise at room temperature to Compound 1 (0.000273 mol) in CH₃CN (5 ml). The mixture was stirred at room temperature for 4 hours. The precipitate was filtered, washed with CH₃CN and dried. Yield: 0.065 g (59%, melting point: >250° C.).

Example 3

Preparation of Compound 3

Compound 3

The same procedure as in example 1 was used, starting from 2-fluoro-6-chloro analog of Intermediate 1 (0.000128 mol) and N-bromosuccinimide (0.000154 mol) in CH₃CN (5 ml), yielding: 0.037 g of Compound 3 (62%, melting point: 236° C.)

Example 4

Preparation of Compound 4

Compound 4

A suspension of CaCO₃ (1.64 g) in water (30 ml) was added to a suspension of intermediate 1 (0.0273 mol) in EtOH (180 ml). Iodine chloride (IC1) in CH₂Cl₂ (1N) (22.5 ml) was added dropwise. The mixture was stirred at room temperature for 24 hours, then cooled to 0° C. and filtered. The filtrate was dried under vacuo, then taken up in EtOH (180 ml), filtered, washed with EtOH and CH₃CN and dried. Yield: 8.5 g. Part of the filtrate was evaporated. The residue was crystallized from hot CH₃CN. The precipitate was filtered off and dried. Yield: 1.54 g (total yield 78%).

Example 5

Preparation of Compounds 5 and 6

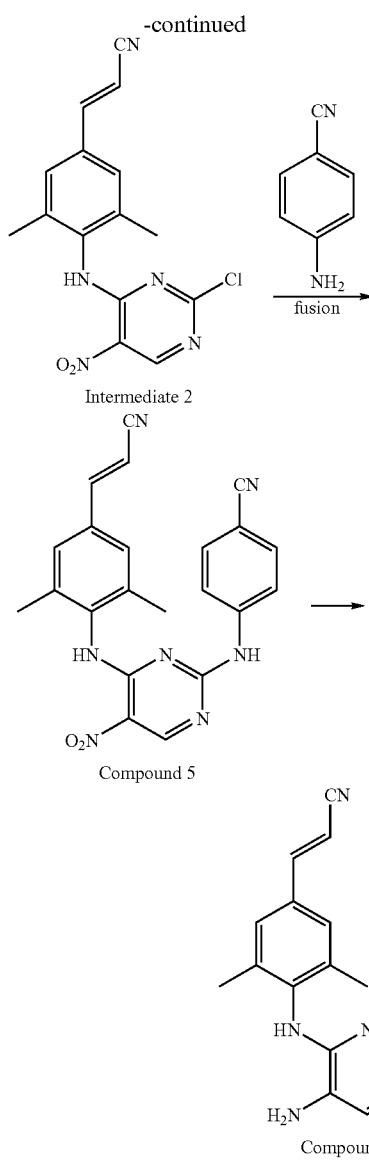

Intermediate 2

Compound 5

Compound 6

A mixture of 2,4-dichloro-5-nitro-pyrimidine (0.0516 mol) and 4-(2-cyanoethenyl)-2,6-dimethylphenylamine (0.0516 mol) were stirred at 140° C. in an oil bath for 45 minutes, then poured in a mixture of water and $K_2CO_3$ 10%. The precipitate was filtered and the filtrate extracted with $CH_2Cl_2$. The organic layer was dried over magnesium sulfate, filtered and the solvent evaporated. The residue was purified by column chromatography over silica gel (eluent: $CH_2Cl_2$100; 35-70 μm). The pure fractions were collected and the solvent evaporated, yield: 6.0 g of intermediate 2 (35%, melting point: >250° C.)

Preparation of Compound 5

A mixture of intermediate 2 (0.0182 mol) and 4-cyanoaniline (0.0182 mol) were heated at fusion for 5 minutes, then poured in a mixture of water and $K_2CO_3$ 10%. $CH_2Cl_2$ and a small quantity of MeOH were added and the precipitate was filtered and dried. Yield: 7.4 g of Compound 5 (95%, melting point: >250° C.)

Preparation of Compound 6

A mixture of Compound 5 (0.0180 mol) and tin (II) chloride dihydrate (0.125 mol) in ethanol (100 ml) were stirred at 70° C. overnigt, then poured in a mixture of water and $K_2CO_3$ 10%. The precipitate was filtered over celite. The filtrate was removed and the precipitate was washed with $CH_2Cl_2$ and THF. The solvent was evaporated. Yield: 6.0 g of compound 6 (87%, melting point: >250° C.).

Example 6

Preparation of the 2-Fluoro-6-Chlorophenyl Analogs of Compounds 5 and 6

A mixture of 2,4-dichloro-5-nitro-pyrimidine (0.0153 mol) and 4-(2-cyanoethenyl)-2-fluoro-6-chloro-phenylamine (0.0153 mol) were heated at fusion for 5 minutes, then poured in a mixture of water and $K_2CO_3$ 10% and extracted with $CH_2Cl_2$. The organic layer was dried over magnesium sulfate, filtered and the solvent evaporated. The residue was purified by column chromatography over silica gel (eluent: $CH_2Cl_2$100; 35-70 μm). The pure fractions were collected and the solvent evaporated. Yield: 1.9 g of 2-chloro-4-[4-(2-cyanoethenyl)-2-fluoro-6-chloro-phenylamino]-5-nitro-pyrimidine, intermediate 3 (35%, melting point: 217° C.).

A mixture of intermediate 3 (0.000424 mol) and 4-cyanoaniline (0.000424 mol) were heated at fusion for 5 minutes, then poured in a mixture of water and $K_2CO_3$ 10%. $CH_2Cl_2$ and a small quantity of MeOH were added and the precipitate was filtered and dried. Yield: 1.34 g of 4-[4-[4-(2-cyanoethenyl)-2-fluoro-6-chloro-phenylamino]-5-nitro-pyrimidine]amino]benzonitrile, Compound 7 (73%, melting point: >250° C.)

A mixture of Compound 7 (0.00306 mol) and tin (II) chloride dihydrate (0.0214 mol) in ethanol (20 ml) were stirred at 70° C. overnight, then poured in a mixture of water and $K_2CO_3$ 10%. The precipitate was filtered over celite. The filtrate was removed and the precipitate was washed with $CH_2Cl_2$ and THF. The solvent was evaporated. Yield: 1.1 g of 4-[4-[4-(2-cyanoethenyl)-2-fluoro-6-chloro-phenylamino]-5-amino-pyrimidine]amino]benzonitrile, Compound 8 (89%, melting point: >250° C.).

Example 7

Preparation of Compound 9

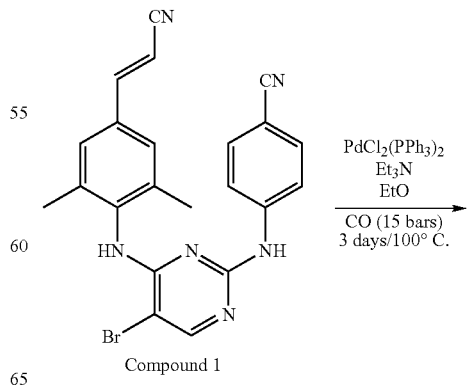

Compound 1

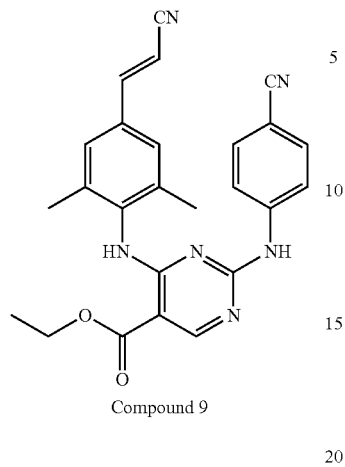

Compound 9

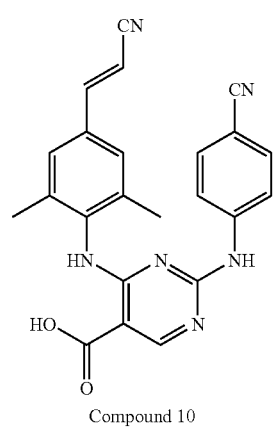

Compound 10

A mixture of compound 1 (0.0247 mol), dichlorobis(triphenylphosphine)-palladium(II) (0.00494 mol) and triethylamine (0.107 mol) in ethanol (100 ml) were stirred at 100° C. for 72 hours under 15 bars pressure of carbon monoxide. The mixture was poured in water. The precipitate was filtered off. Yielding: 6 g. The filtrate was extracted with $CH_2Cl_2$. The organic layer was dried over magnesium sulfate, filtered and the solvent was evaporated. The residue was purified by column chromatography over silica gel (eluent: $CH_2Cl_2$/MeOH 99.5/0.5; 15-40 μm). The pure fractions were collected and the solvent evaporated. Yield: 1.9 g. The two fractions were collected. Total yield: 7.9 g of Compound 2 (73%, melting point: >250° C.). Compound 26 was prepared from compound 3, using the same procedures.

A mixture of Compound 9 (0.00456 mol), lithium hydroxide, monohydrate (0.0137 mol) in THF (20 ml) and water (7 ml) were stirred at 50° C. overnight. The THF was evaporated. The residue was diluted in water and HCl 3N was added until pH 2-3. The precipitate was filtered off, washed with water and dried. Yield: 1.78 g of compound 10 (95%, melting point: >250° C.).

Example 8

Preparation of Compound 10

Example 9

Preparation of Compound 11

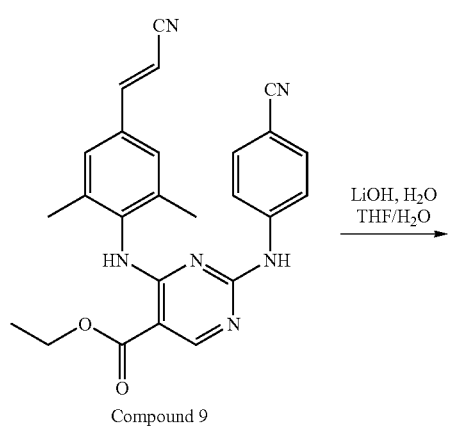

Compound 9

LiOH, H₂O
THF/H₂O →

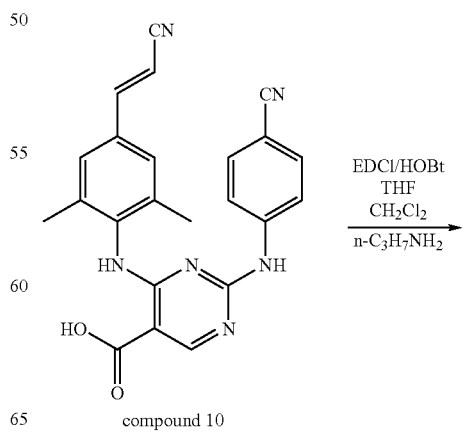

compound 10

EDCl/HOBt
THF
$CH_2Cl_2$
───────→
n-C₃H₇NH₂

Example 10

Preparation of Compound 12

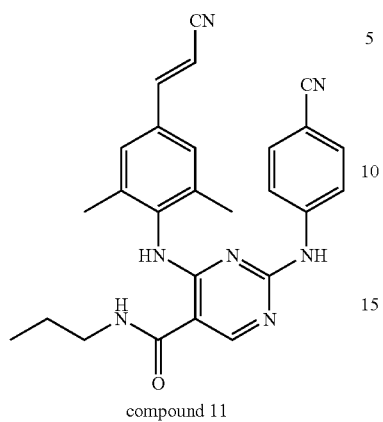
compound 11

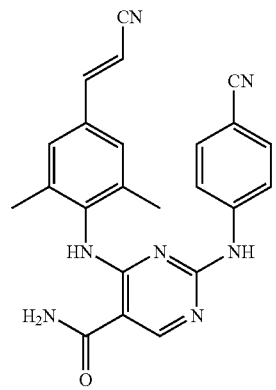 [SMILES: Cc1cc(/C=C/C#N)cc(C)c1Nc1nc(Nc2ccc(C#N)cc2)ncc1C(N)=O]

1-hydroxybenzotriazole (0.548 mmol) was added to a mixture of compound 10 (0.365 mmol) in THF (3 ml). Dichloromethane (3 ml) and 1-(3-dimethylaminopropyl)-3-ethyl-carbodiimide hydrochloride (0.548 mmol) were added successively to the mixture. To this solution, 1-propylamine (0.548 mmol) was added. The mixture was stirred at room temperature for 24 h then poured in water and $K_2CO_3$ 10% and extracted with a 90/10 mixture of $CH_2Cl_2$ and methanol. The organic layer was washed with a solution of brine, dried over magnesium sulfate, filtered and the solvent evaporated. The residue was purified by column chromatography over silica gel (eluent: $CH_2Cl_2$ 100 to $CH_2Cl_2$/MeOH 95/5; Kromasil 5 µm). Yield: 0.116 g. of Compound 11 (70%, melting point: >250° C.).

Compound 30 was prepared using the same procedures, starting from compound 3.

Thionyl chloride (5 ml) was added to Compound 10 (0.000365 mol) and the mixture was heated to reflux for 1 hour. Thionyl chloride was removed in vacuo and the residue was diluted in $CH_2Cl_2$ (5 ml). The mixture was cooled at 0° C. and ammonia 30% (2 ml) was added drop wise. The mixture was stirred at 0° C. at least 1 hour and the precipitate was filtered off, washed with water and diisopropyl-ethylether and dried. The residue was purified by column chromatography over silica gel (eluent: $CH_2Cl_2$/MeOH/$NH_4OH$ 95/5/0.1; 35-70 µm). The pure fractions were collected and the solvent evaporated. Yield: 0.071 g of Compound 12 (47%, melting point: >250° C.).

Example 11

Preparation of Compounds 13, 14, and 15

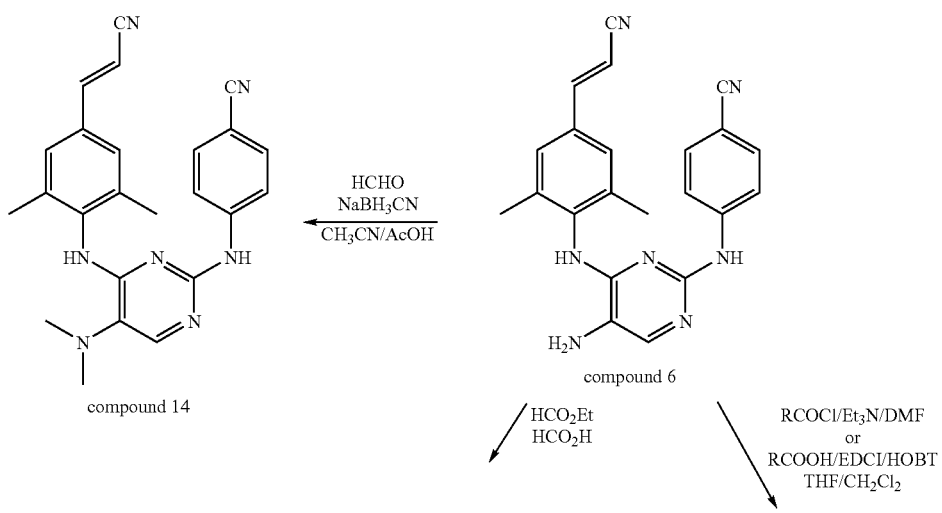

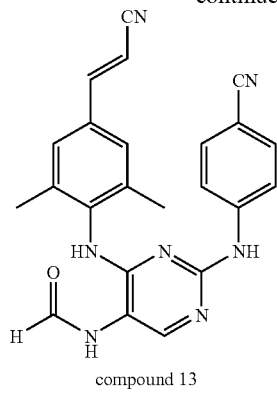

compound 13

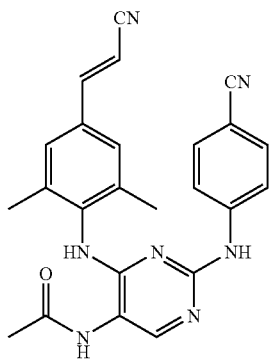 [SMILES: CC(=O)Nc1cnc(Nc2ccc(C#N)cc2)nc1Nc1c(C)cc(/C=C/C#N)cc1C]

R is methyl
compound 15

Formic acid (10 ml) was added at room temperature to Compound 6 (0.00215 mol) in ethyl formate (30 ml). The mixture was stirred at reflux 4 hours. The mixture was evaporated till dryness, then poured in water and $K_2CO_3$ 10% and extracted with $CH_2Cl_2$ and MeOH. The organic layer was dried over magnesium sulfate, filtered and the solvent evaporated. The residue was crystallized from $CH_2Cl_2$ and MeOH. Yield: 0.48 g of Compound 13 (55%, melting point: >250° C.).

Preparation of Compound 14

Sodium cyanoborohybride (0.00262 mol) was added at room temperature to a mixture of Compound 6 (0.000524 mol) and paraformaldehyde (0.00524 mol) in acetonitrile (10 ml). A few drops of acetic acid were added and the mixture was stirred at room temperature for 2 hours. The mixture was poured into water and $K_2CO_3$ 10% and extracted with $CH_2Cl_2$. The organic layer was dried over magnesium sulfate, filtered and the solvent evaporated. The residue was purified by column chromatography over silica gel (eluent: $CH_2Cl_2$ 100 to $CH_2Cl_2$/MeOH 99/1; 10 μm). The pure fractions were collected and the solvent evaporated. Yield: 0.070 g. This fraction was crystallized from diisopropyl-ethylether. The precipitate was filtered off and dried. Yield: 0.059 g of Compound 14 (27%, melting point: >250° C.).

Preparation of Compound 15

Acetyl chloride (0.000315 mol) was added drop wise at room temperature to a mixture of Compound 6 (0.000262 mol) and triethylamine (0.000524 mol) in $CH_2Cl_2$ (2 ml) and THF (2 ml). The mixture was stirred at room temperature for 4 hours, then poured in water and $K_2CO_3$ 10% and extracted with $CH_2Cl_2$. The organic layer was dried over magnesium sulfate, filtered and the solvent evaporated. The residue was purified by column chromatography over silica gel (eluent: $CH_2Cl_2$/MeOH/$NH_4OH$ 95/5/0.1; 35-70 μm). The pure fractions were collected and the solvent evaporated. Yield: 0.061 g of Compound 15 (55%, melting point >250° C.). Compound 28 was prepared following the same procedures and starting from compound 8.

Example 12

Preparation of 5-Aryl Compounds

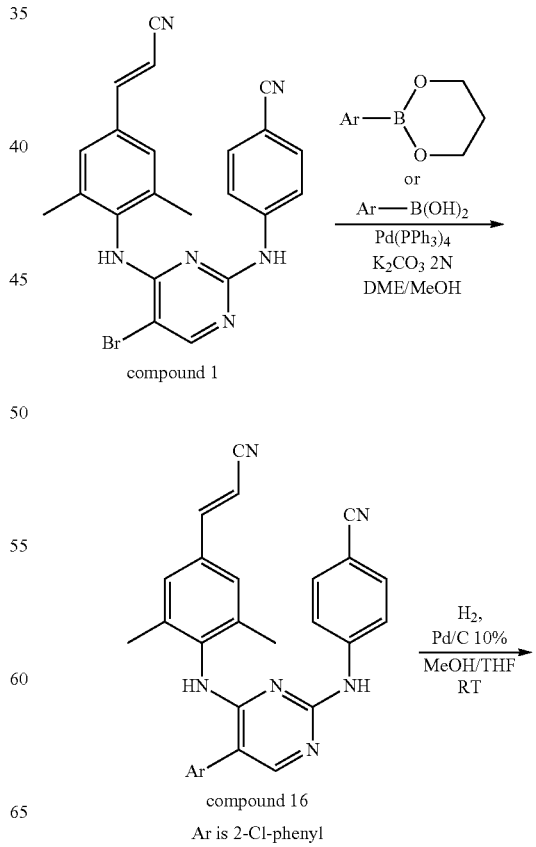

compound 16

Ar is 2-Cl-phenyl

-continued

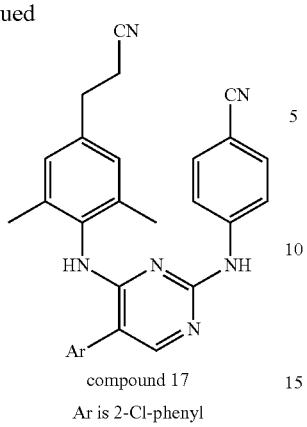
compound 17
Ar is 2-Cl-phenyl point: 168-170° C.). Compound 17 is prepared by reacting compound 16 with hydrogen in the presence of Pd/C in a methanol/THF mixture.

Example 13

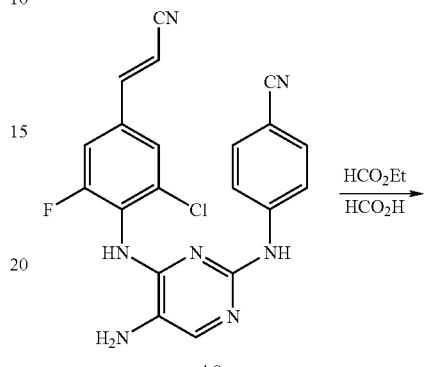
compound 8

$\xrightarrow{\text{HCO}_2\text{Et}}{\text{HCO}_2\text{H}}$

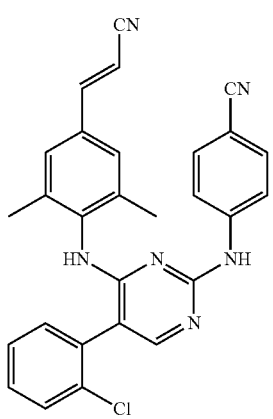

Compound 1 (0.449 mmol) was added to a solution of tetrakis(triphenylphosphine)-palladium(0) (0.0449 mmol) in 1,2-dimethoxyethane at room temperature. A solution of 2-chlorophenylboronic acid (0.135 mmol) in methanol (3 ml) was added at room temperature. The mixture was stirred at 95° C. for 24 h and was then poured in water, extracted with ethyl acetate. The organic layer was washed with a brine solution and dried over magnesium sulfate, filtered and evaporated. The residue was purified by column chromatography over silica gel (eluent: CH$_2$Cl$_2$/MeOH 99/1; Kromasil Si 10 µm). The pure fractions were collected and the solvent evaporated. Yield: 0.130 g of compound 16 (60%, melting

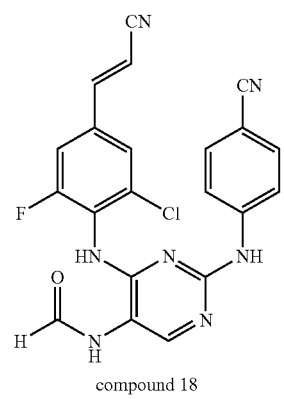
compound 18

Preparation of Compound 18

Formic acid (2 ml) was added at room temperature to Compound 8 (0.000370 mol) in ethyl formate (6 ml). The mixture was stirred at reflux 3 hours. The mixture was poured in water and K$_2$CO$_3$ 10%. The precipitate was filtered, washed with diisopropyl-ethylether and dried. The residue was crystallized from CH$_2$Cl$_2$ and MeOH. Yield: 0.72 g of Compound 18 (45%, melting point: 250° C.).

Example 14

Preparation of Compound 19

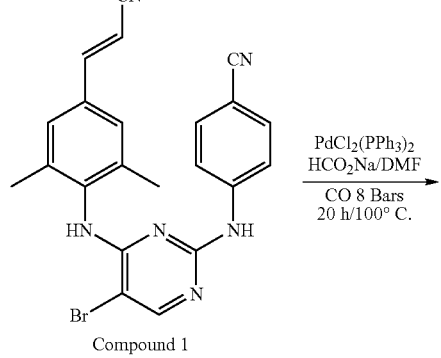

Compound 1

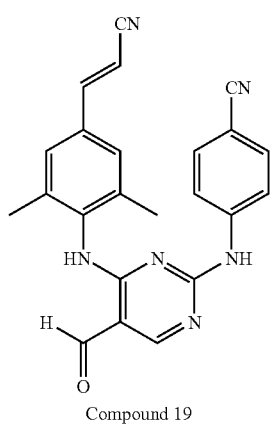

Compound 19

A mixture of Compound 1 (0.0112 mol), dichlorobis(triphenylphosphine)-palladium(II) (0.00228 mol), sodium formate (0.0336 mol) and magnesium sulfate (1 g) in DMF (50 ml) were stirred at 100° C. for 20 hours under 8 bars pressure of carbon monoxide. The mixture was filtered over celite and poured in water. The precipitate was filtered off, washed with water and Et$_2$O and dried. Yield: 2.9 g. of Compound 19 (65%, melting point: >250° C.).

Example 15

Preparation of Compound 20

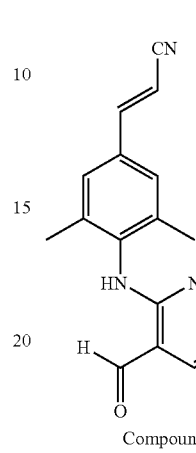

Compound 19

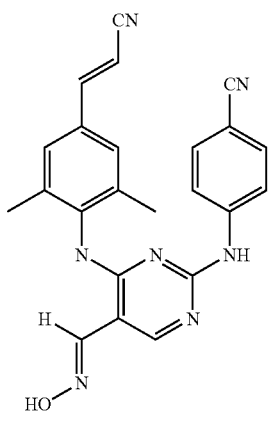

Compound 20

A mixture of Compound 19 (0.000254 mol) and hydroxylamine hydrochloride (0.000380 mol) in pyridine (3 ml) was stirred at room temperature for 20 hours, then poured in water. The precipitate was filtered off, washed with water and Et$_2$O and dried. Yield: 0.048 g. of Compound 20 (39%, melting point: >250° C.).

Example 16

Preparation of Compound 31

A suspension of Compound 19 (0.0003 mol) and methoxyamine hydrochloride (0.0004 mol) in pyridine (4 ml) was stirred at room temperature overnight, poured out into water, filtered, washed with water and dried at 85° C. under vacuum. The residue (0.128 g) was purified by column chromatography over kromasil, eluent: CH$_2$Cl$_2$/CH$_3$OH 100/0 to 95/5; 5 μm). The pure fractions were collected and the solvent was evaporated, yielding: 0.065 g (46%) of Compound 31 (melting point >250° C.)

Example 17

Preparation of Compound 26

A mixture of Compound 12 (0.0001 mol) and Pd/C 10% (0.1 g) in THF (5 ml) and MeOH (5 ml) was hydrogenated at room temperature overnight under 3 bar pressure, then filtered over celite. The filtrate was evaporated. The residue was crystallized from DIPE. The precipitate was filtered off and dried, yielding: 0.065 g (81%) of Compound 26 (melting point: 180° C.).

Example 18

Preparation of Compound 33

A mixture of Compound 6 (0.0005 mol) and Pd/C 10% (0.2 g) in THF (8 ml) and MeOH (6 ml) was hydrogenated at room temperature overnight under a 3 bar pressure, then filtered over celite. The filtrate was evaporated. This fraction was purified by column chromatography over silica gel (eluent: CH₂Cl₂/CH₃OH 95/5; 35-70 μm). The pure fractions were collected and the solvent was evaporated. Yield: 0.071 g (35%) (melting point: 180° C.).

The following tables list compounds which were or can be prepared according to the procedures described in the above examples.

TABLE 1

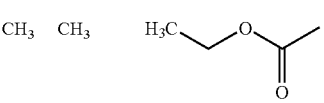

| Comp. no. | Example | R³ | R⁴ | R⁵ | Phys. Data and stereo-chemistry |
|---|---|---|---|---|---|
| 1 | 1 | CH₃ | CH₃ | Br | >250° C. |
| 2 | 2 | CH₃ | CH₃ | Cl | >250° C. |
| 3 | 3 | F | Cl | Br | 236° C. |
| 4 | 4 | CH₃ | CH₃ | I | >250° C. |
| 5 | 5 | CH₃ | CH₃ | NO₂ | >250° C. |
| 6 | 5 | CH₃ | CH₃ | NH₂ | >250° C. |
| 7 | 6 | F | Cl | NO₂ | >250° C. |
| 8 | 6 | F | Cl | NH₂ | >250° C. |
| 9 | 7 | CH₃ | CH₃ | 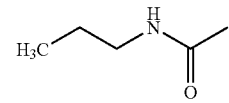 | >250° C. |
| 10 | 8 | CH₃ | CH₃ | —COOH | >250° C. |
| 11 | 9 | CH₃ | CH₃ | 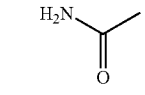 | >250° C. |
| 12 | 10 | CH₃ | CH₃ | 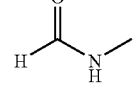 | (E) >250° C. |
| 13 | 11 | CH₃ | CH₃ | 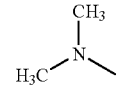 | >250° C. |
| 14 | 11 | CH₃ | CH₃ | 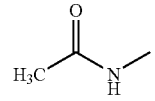 | >250° C. |
| 15 | 11 | CH₃ | CH₃ |  | >250° C. |

TABLE 1-continued
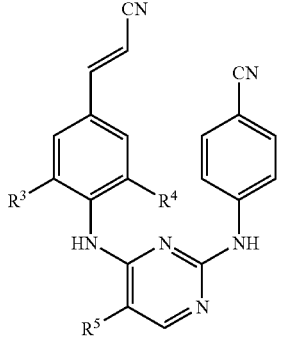
| Comp. no. | Example | R³ | R⁴ | R⁵ | Phys. Data and stereo-chemistry |
|---|---|---|---|---|---|
| 16 | 12 | CH₃ | CH₃ | 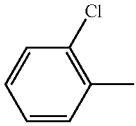 | 168-170° C. |
| 18 | 13 | F | Cl | 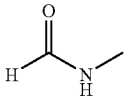 | 250° C. |
| 19 | 14 | CH₃ | CH₃ | —COH | >250° C. |
| 20 | 15 | CH₃ | CH₃ | 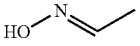 | >250° C. |
| 21 | 9 | CH₃ | CH₃ | 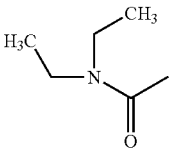 | (E) 225° C. |
| 22 | 9 | CH₃ | CH₃ | 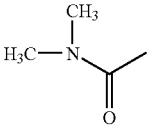 | (E/Z:96/4) >250° C. |
| 23 | 9 | CH₃ | CH₃ | 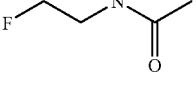 | (E) >250° C. |
| 24 | 9 | CH₃ | CH₃ | 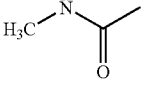 | (E) >250° C. |
| 25 | 9 | CH₃ | CH₃ | 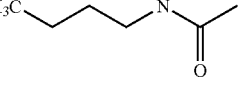 | (E) 241° C. |
| 27 | 12 | CH₃ | CH₃ | 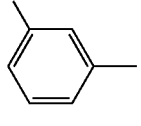 | 150-152° C. |

TABLE 1-continued

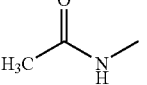

| Comp. no. | Example | R³ | R⁴ | R⁵ | Phys. Data and stereo-chemistry |
|---|---|---|---|---|---|
| 28 | 11 | F | Cl | 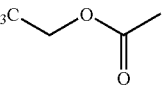 | (E) >250° C. |
| 29 | 12 | F | Cl | 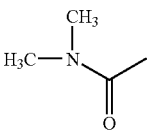 | (E) >244° C. |
| 30 | 9 | F | Cl | 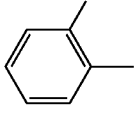 | (E/Z:90/10) 243° C. |
| 31 | 16 | CH₃ | CH₃ | C₂H₅—O—N=CH— | (E) >250° C. |
| 32 | 16 | CH₃ | CH₃ | CH₃—O—N=CH— | (E) >250° C. |

TABLE 2

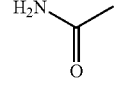

| Comp. no. | Example | R³ | R⁴ | R⁵ | Phys. Data and stereochemistry |
|---|---|---|---|---|---|
| 17 | 12 | CH₃ | CH₃ | 2-Cl-phenyl | |
| 26 | 19 | CH₃ | CH₃ | H₂N-C(=O)- | 180° C. |
| 33 | 20 | CH₃ | CH₃ | NH₂ | 180° C. |

Formulation Examples

Capsules

A compound of formula (I) is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxyl-propylmethylcellulose (HPMC), typically 5 mPa·s, are dissolved in organic solvents such as ethanol, methanol methylene chloride. Suitably the polymer is dissolved in ethanol. The polymer and compound solutions are mixed and subsequently spray dried. The ratio of compound/polymer is selected from 1/1 to 1/6. Intermediate ranges can be 1/1.5 and 1/3. A suitable ratio can be 1/6. The spray-dried powder, a solid dispersion, is subsequently filled in capsules for administration. The drug load in one capsule ranges between 50 and 100 mg depending on the capsule size used.

Film-coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenized. The tablet cores are coated with the thus obtained mixture in a coating apparatus.

Antiviral Spectrum:

Because of the increasing emergence of drug resistant HIV strains, the present compounds were tested for their potency against clinically isolated HIV strains harboring several mutations. These mutations are associated with resistance to reverse transcriptase inhibitors and result in viruses that show various degrees of phenotypic cross-resistance to the currently commercially available drugs such as for instance AZT and delavirdine.

The antiviral activity of the compound of the present invention has been evaluated in the presence of wild type HIV and HIV mutants bearing mutations at the reverse transcriptase gene. The activity of the compounds is evaluated using a cellular assay and the residual activity is expressed in $pEC_{50}$ values. The columns IIIB and A-G in the table list the $pEC_{50}$ values against various strains IIIB, A-G.

Strain IIIB is wild type HIV-LAI strain

Strain A contains mutation Y181C in HIV reverse transcriptase,

Strain B contains mutation K103N in HIV reverse transcriptase,

Strain C contains mutation L100I in HIV reverse transcriptase,

Strain D contains mutation Y188L in HIV reverse transcriptase,

Strain E contains mutations L100I and K103N in HIV reverse transcriptase,

Strain F contains mutations K103N and Y181C in HIV reverse transcriptase, and

Strain G contains mutations L100I, K103N, Y181C, V179I, Y181C, E138G, V179I, L2214F, V278V/1 and A327A/V in HIV reverse transcriptase.

| Compound number | IIIB | A | B | C | D | E | F | G |
|---|---|---|---|---|---|---|---|---|
| 26 | 9.7 | 9 | 9.7 | 10 | 8.6 | 9.2 | 9.2 | 6.4 |
| 13 | 9.4 | 8.6 | 9.2 | 9.2 | 8.5 | 8.2 | 8.4 | 6 |
| 27 | 7.9 | 3.3 | 7.9 | 7.3 | 6.5 | 6.5 | 6.6 | 4.6 |
| 28 | 8.8 | 7.9 | 8.6 | 8.3 | 7.3 | 7 | 7.3 | 4.7 |
| 29 | 8.4 | 7 | 8.2 | 7.7 | 6.2 | 7 | 6.4 | 4.6 |
| 30 | 7.7 | 7.3 | 7.2 | 6.9 | 6.5 | 6.4 | 6.5 | 5 |
| 31 | 8.5 | 8.2 | 8.5 | 8.5 | 8.2 | 8.2 | 8.2 | 5.1 |
| 32 | 8.5 | 8.5 | 8.7 | 9.3 | 8.6 | 8.6 | 8.7 | 6 |

The invention claimed is:

1. A compound of formula

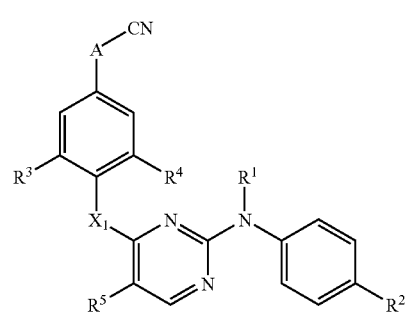

(I)

a N-oxide, a pharmaceutically acceptable addition salt, a quaternary amine or a stereochemically isomeric form thereof, wherein A is —$CH_2$—$CH_2$—, —CH=CH—, —C≡C—;

each $R^1$ independently is hydrogen, aryl, formyl, $C_{1-6}$alkylcarbonyl, $C_{1-6}$alkyl, $C_{1-6}$alkyloxycarbonyl;

$R^2$ is hydroxy, halo, $C_{1-6}$alkyl, carboxyl, cyano, —C(=O)$R^6$, nitro, amino, mono- or di($C_{1-6}$ alkyl)amino, polyhalomethyl;

$X_1$ is —$NR^1$—, —O—, —S—, —S(=O)$_p$—;

$R^3$ is H, $C_{1-6}$alkyl, halo;

$R^4$ is H, $C_{1-6}$alkyl, halo;

$R^5$ is nitro, amino, mono- and di$C_{1-4}$ alkylamino, halo, —CO—H, —CO—$R^6$, —$COOR^7$, —NH—C(=O)H, —CH=N—O—$R^8$;

$R^6$ is $C_{1-4}$alkyl, amino, mono($C_{1-4}$alkyl)amino or polyhalo$C_{1-4}$alkyl;

$R^7$ is hydrogen, aryl$C_{1-6}$alkyl;

$R^8$ is hydrogen, $C_{1-6}$alkyl, aryl;

each p is 1 or 2;

each aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl.

2. A compound according to claim 1 wherein
A is —$CH_2$—$CH_2$— or —CH=CH—;
$R^1$ is hydrogen or $C_{1-6}$alkyl;
$R^2$ is cyano or aminocarbonyl;
$X_1$ is —$NR^1$—, —O—;
$R^3$ is H, $C_{1-6}$alkyl, halo;
$R^4$ is H, $C_{1-6}$alkyl, halo.

3. A compound according to claim 1 wherein
$R^6$ is $C_{1-4}$alkyl, amino, or mono($C_{1-4}$alkyl)amino;
$R^7$ is hydrogen;
$R^8$ is hydrogen, $C_{1-4}$alkyl;
aryl is phenyl or phenyl substituted with one, two or three substituents each independently selected from halo, hydroxy, mercapto, $C_{1-6}$ alkyl, hydroxy$C_{1-6}$ alkyl, amino$C_{1-6}$ alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl.

4. A compound according to claim 1 wherein
A is —$CH_2$—$CH_2$— or —CH=CH—;
$R^1$ is hydrogen;

R² is cyano;
X₁ is —NH— or —O—;
R³ is H, $C_{1-4}$alkyl, halo;
R⁴ is H, $C_{1-4}$alkyl, halo.

5. A compound according to claim 1 wherein
R⁶ is $C_{1-4}$alkyl, or amino;
R⁷ is hydrogen;
R⁸ is hydrogen, $C_{1-4}$alkyl;
aryl is phenyl or phenyl substituted with one, two or three substituents each independently selected from halo, hydroxy, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, trifluoromethyl, trifluoromethoxy, aminocarbonyl.

6. A compound according to claim 1 wherein A is —CH═CH—; X₁ is —NH—;
R³ is methyl or halo; R⁴ is methyl or halo; R⁶ is amino.

7. A compound according to claim 1 wherein
R⁵ is nitro; or
R⁵ is amino; mono- and di $C_{1-4}$alkylamino; —NH—C(═O)H.

8. A compound according to claim 1 wherein
R⁵ is halo.

9. A compound according to claim 1 wherein
R⁵ is —CO—H, —CO—R⁶, —COOR⁷.

10. A compound according to claim 1 wherein
R⁵ is —CH═N—O—R⁸.

11. A compound according to claim 1, wherein R⁵ is amino or mono- and di-$C_{1-4}$alkylamino.

12. A compound according to claim 1, wherein R⁸ is hydrogen or $C_{1-4}$alkyl.

13. A pharmaceutical composition comprising a pharmaceutically acceptable carrier and as active ingredient a therapeutically effective amount of a compound as claimed in claim 1.

14. A process for preparing a pharmaceutical composition comprising a pharmaceutically acceptable carrier and as active ingredient a therapeutically effective amount of a compound as claimed in claim 1 characterized in that a therapeutically effective amount of a compound as claimed in claim 1 is intimately mixed with a pharmaceutically acceptable carrier.

15. A method for treating HIV infection comprising:
administering a compound according to claim 1 to a patient in need thereof.

* * * * *